US011129958B2

(12) United States Patent  
Xie et al.

(10) Patent No.: US 11,129,958 B2  
(45) Date of Patent: Sep. 28, 2021

(54) SLEEP-INDUCING DEVICE

(71) Applicant: Shenzhen Aeon Technology Co., Ltd., Shenzhen (CN)

(72) Inventors: Hua Xie, Shenzhen (CN); Li Ju, Shenzhen (CN)

(73) Assignee: SHENZHEN AEON TECHNOLOGY CO., LTD., Shenzhen (CN)

( * ) Notice: Subject to any disclaimer, the term of this patent is extended or adjusted under 35 U.S.C. 154(b) by 188 days.

(21) Appl. No.: 16/535,059

(22) Filed: Aug. 7, 2019

(65) Prior Publication Data

US 2020/0101261 A1    Apr. 2, 2020

(30) Foreign Application Priority Data

Sep. 27, 2018 (CN) .......................... 201811132005.4

(51) Int. Cl.  
*A61M 21/02* (2006.01)  
*A61M 21/00* (2006.01)

(52) U.S. Cl.  
CPC ..... *A61M 21/02* (2013.01); *A61M 2021/0027* (2013.01); *A61M 2021/0061* (2013.01)

(58) Field of Classification Search  
CPC ...... A61M 2230/06; A61M 2021/0061; A61M 21/02; A61M 2205/8206  
See application file for complete search history.

(56) References Cited

U.S. PATENT DOCUMENTS

2011/0036801 A1*  2/2011  Krans .................. A61J 9/00  
                                                 215/11.1  
2015/0250978 A1*  9/2015  Pelsue ................. A61M 21/02  
                                                 600/28  
2018/0360326 A1* 12/2018  Lee .................... H01M 10/44

* cited by examiner

*Primary Examiner* — Christine H Matthews  
(74) *Attorney, Agent, or Firm* — Matthias Scholl P.C.; Matthias Scholl

(57) ABSTRACT

A sleep-inducing device, including: 1) a probe including a heart rate sensor detecting a heart rate of an infant's mother; 2) a sampling module collecting data with regard to the heart rate detected by the probe; 3) a first microcontroller unit (MCU) calculating the data transmitted from the sampling module and outputting a heart rate signal; 4) a second microcontroller unit (MCU) receiving and processing the heart rate signal transmitted from the first MCU; 5) a keyboard inputting, controlling and adjusting parameters of the second MCU; 6) a display displaying an operation/control state of the device; 7) a loudspeaker playing audio data of the heart rate signal processed by and transmitted from the second MCU; 8) a first memory storing the audio data of the heart rate signal; 9) a low dropout regulator (LDO) providing a constant voltage to the second MCU; and 10) a power supply.

18 Claims, 1 Drawing Sheet

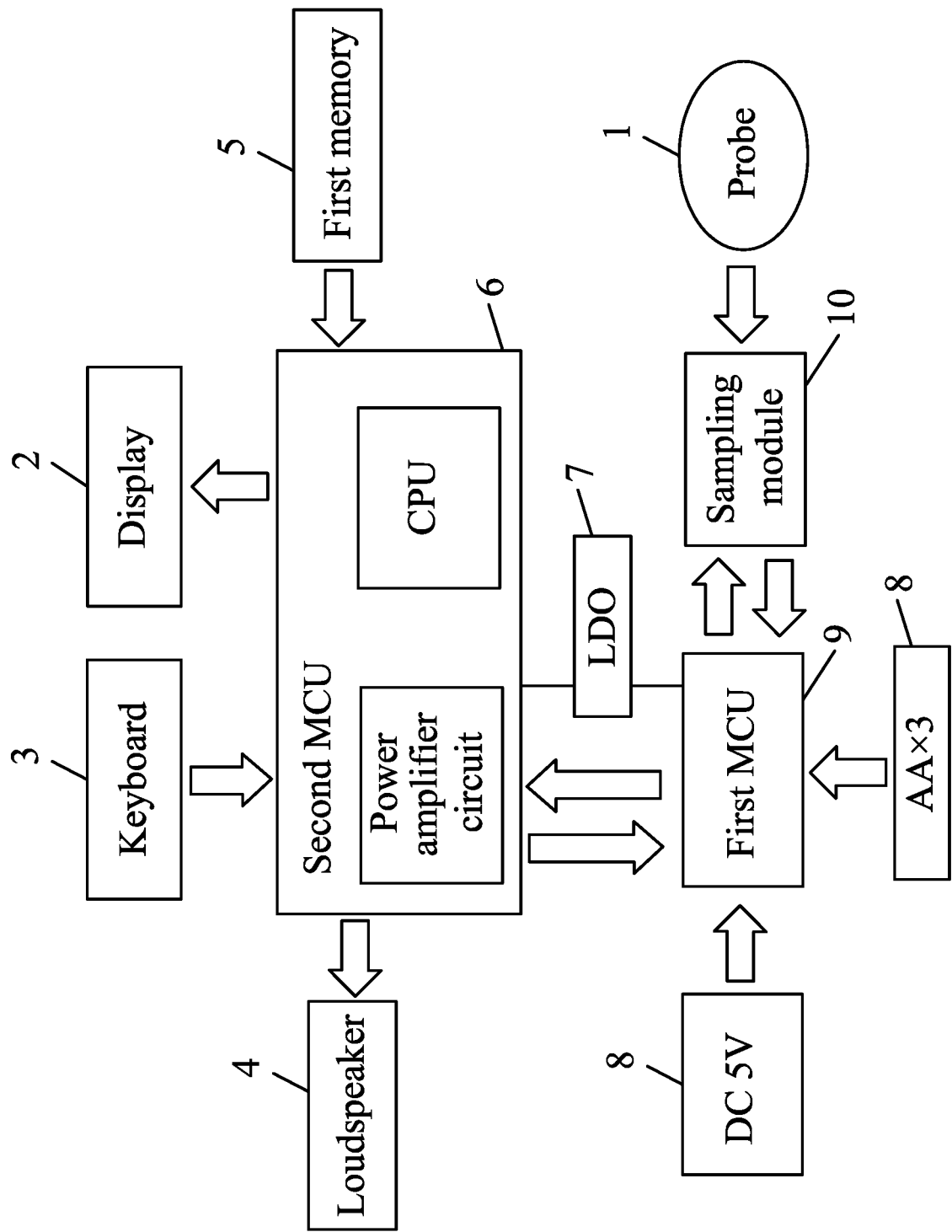

SLEEP-INDUCING DEVICE

CROSS-REFERENCE TO RELATED APPLICATIONS

Pursuant to 35 U.S.C. § 119 and the Paris Convention Treaty, this application claims foreign priority to Chinese Patent Application No. 201811132005.4 filed Sep. 27, 2018, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a sleep-inducing device, and more particularly to a device for pacifying an infant to sleep.

Digital sleep-inducing devices are known that help to induce deep sleep by playing prerecorded soothing music and soft nature sounds. The problem with such devices is that they have a fixed frequency and rhythm and users tend to get tired of them.

SUMMARY

The disclosure discloses a sleep-inducing device which can sense the heart rate of an infant's mother in real-time and pacify the infant.

Provided is a sleep-inducing device comprising:
1) a probe comprising a heart rate sensor detecting a heart rate of an infant's mother;
2) a sampling module collecting data with regard to the heart rate detected by the probe;
3) a first microcontroller unit (MCU) calculating the data transmitted from the sampling module and outputting a heart rate signal;
4) a second microcontroller unit (MCU) receiving and processing the heart rate signal transmitted from the first MCU;
5) a keyboard inputting, controlling and adjusting parameters of the second MCU;
6) a display displaying an operation/control state of the device;
7) a loudspeaker playing audio data of the heart rate signal processed by and transmitted from the second MCU;
8) a first memory storing the audio data of the heart rate signal processed by and transmitted from the second MCU;
9) a low dropout regulator (LDO) providing a constant voltage to the second MCU; and
10) a power supply supplying power to components in 1)-9).

The heart rate sensor is a blood oxygen sensor, a photoplethysmography sensor, an electrocardiogram sensor, or an arterial blood pressure sensor.

The power supply is a DC 5V adaptor or an alkaline battery.

The first MCU comprises a CPU and an analog-to-digital (AD) conversion circuit to calculate the data of the heart rate transmitted from the sampling module; the AD conversion circuit converts an electrical signal detected by the probe into a digital signal recognizable to the first MCU.

The second MCU comprises a CPU, a second memory, a sound processing circuit, and a power amplifier circuit; the heart rate signal transmitted from the first MCU is temporarily stored in the second memory, transformed by the sound processing circuit, and output to the display; the power amplifier circuit is directly connected to the loudspeaker.

The second memory is a FLASH, a SD card, or a disc.

The power amplifier circuit is electrically connected to the loudspeaker via a wire.

The second MCU comprises an interface communicating with an additional probe.

The second MCU comprises a wireless receiver to communicate with wireless equipment.

Compared with the prior art, advantages of the sleep-inducing device according to embodiments of the disclosure are summarized as follows. The sleep-inducing device comprise a sensor capable of collecting a mother's real heart rate. The real heart rate is converted into an audio signal broadcasted by a loudspeaker to pacify an infant to fall asleep. The device is easy to operate.

BRIEF DESCRIPTION OF THE DRAWINGS

The invention is described hereinbelow with reference to accompanying drawings, in which the sole FIGURE is a schematic diagram of a sleep-inducing device.

In the drawings, the following reference numbers are used: 1. Probe; 2. Display; 3. Keyboard; 4. Loudspeaker; 5. First memory; 6. Second MCU; 7. Low dropout regulator (LDO); 8. Power supply; 9. First MCU; 10. Sampling module.

DETAILED DESCRIPTION

To further illustrate the invention, experiments detailing a sleep-inducing device are described below. It should be noted that the following examples are intended to describe and not to limit the invention.

Example 1

As shown in FIG. 1, the device comprises a probe 1, a display 2, a keyboard 3, a loudspeaker 4, a first memory 5, a second MCU 6, a low dropout regulator (LDO) 7, a power supply 8, a first MCU 9, and a sampling module 10.

The probe 1 comprises a heart rate sensor to detect the heart rate of the infant's mother. The probe is of a blood oxygen type, a photoelectric volume type, an electrocardiographic signal type or an arterial blood pressure type.

The display 2 displays an operation/control state.

The keyboard 3 controls and adjusts various components inside the second MCU6.

The loudspeaker 4 plays data processed by the second MCU 6.

The first memory 5 stores data processed by the second MCU 6 and audio data.

The second MCU 6 display heart rate signals transmitted by the first MCU 9.

The low dropout regulator 7 provides a stable voltage to the first MCU 9.

The power supply 8 employs a DC 5V adaptor or AA×3 alkaline battery.

The first MCU 9 calculates the data of the sampling module 10 and outputs the heart rate signal to the second MCU 6.

The sampling module 10 process the heart rate collected from the probe 1.

The probe 1 may be one of a blood oxygen type, a photoelectric volume type, an electrocardiographic signal type or an arterial blood pressure type.

The second MCU 6 comprises a CPU, a second memory, a sound processing circuit, and a power amplifier circuit; the heart rate signal transmitted from the first MCU is temporarily stored in the second memory, transformed by the sound processing circuit, and output to the display; the power amplifier circuit is directly connected to the loudspeaker.

The first MCU 9 comprises a CPU and an analog-to-digital (AD) conversion circuit to calculate the data of the heart rate transmitted from the sampling module; the AD conversion circuit converts an electrical signal detected by the probe into a digital signal recognizable to the first MCU.

The AD conversion circuit converts an electric signal detected by probe into a digital signal recognized by the first MCU 9.

The power amplifier circuit, which is an amplifying circuit for outputting a larger power, is directly connected to and drive the loudspeaker 4.

The sound processing circuit is configured to decode and synthesize the audio data.

One side of the second MCU 6 is provided with an interface. Through the interface, the second MCU 6 is connected to an additional probe 1.

The battery is fixed inside the infant sleep-inducing device with a bolt, and a power interface is located closely to the battery where is at an outer surface of the infant sleep-inducing device.

A wire is arranged between the power amplifier circuit and the loudspeaker 4, and the power amplifier circuit is electrically connected to the loudspeaker 4 via the wire.

A wireless receiver is disposed in the second MCU, and the wireless receiver is in communication with a device such as a mobile phone.

The main sources of sound for the existing infant sleep-inducing device is stream/light rain/summer night/tide/fan/white noise and pre-recorded heartbeat. Simulating the infant's environment in the mother's abdomen by playing the sound via the playback device, which makes infant easier to fall asleep. There are certain drawbacks when using existing infant sleep-inducing device. The sound of pre-recorded heartbeat, which is only played in a fixed frequency, may not truly reflect a mother's heartbeat.

When the heart rate sensor is of a blood oxygen type, the algorithm for determining the blood oxygen saturation level is described as follows.

Oxyhemoglobin HbO2 and reduced hemoglobin Hb in adult blood have different absorption coefficients for light of different wavelengths. The absorption coefficient of Hb is 10 times that of HbO2 in the red (RED) region with a wavelength of 660 nm; but the absorption efficient of Hb is smaller than that of HbO2 in the infrared (IR) region with a wavelength of 940 nm; and the equal absorption point is around at 805 nm.

Both of these light absorptions have a pulsating part. The arterial pulsation enhances the light signaling pathway and the absorption, forming a light absorption wave (AC), while the light intensity (DC) absorbed by other tissues remains relatively stable. From this, the light absorption ratio (R) of the two wavelengths is calculated, as follows:

$$R = \frac{AC660\,nm/DC\,660\,nm}{AC940\,nm/DC\,940\,nm};$$

R is negatively correlated with blood oxygen saturation SPO2, and the corresponding SPO2 value is obtained by the scale curve. The photoelectricity is measured by photoelectric technology according to Lambert-Beer Law. When light passes through the blood, there is the following relationship between the transmitted light intensity I and the emitted light intensity $I_0$: $I(\lambda, t) = I_0 \exp(-(SEO(\lambda)+(1-S)Er(\lambda))L(t))$, S is the blood oxygen saturation, $\lambda$ is the light wavelength, $I_0$ is the intensity of incident light in blood, $EO(\lambda)$ and $Er(\lambda)$ are absorption coefficients of oxyhemoglobin HbO2 and reduced hemoglobin Hb for incident light at wavelength $\lambda$, respectively, and L is an optical path.

Calculate and get the formula for blood oxygen saturation. The formula should be linear, which means that it needs to compensate by using the squares method because of the scattering properties of the human body: $SaO2 = K_1 R^2 + K_2 R + K_3$, where $K_1$, $K_2$, and $K_3$ in this formula are empirical constants.

Example 2

As shown in FIG. 1, the device comprises a probe 1, a display 2, a keyboard 3, a loudspeaker 4, a first memory 5, a second MCU 6, a low dropout regulator 7, a power supply 8, a first MCU 9, a sampling module 10.

The probe 1 comprises a heart rate sensor to detect the heart rate of the infant's mother, may be one of a blood oxygen type, a photoelectric volume type, an electrocardiographic signal type or an arterial blood pressure type.

The display 2 displays an operation/control state.

The keyboard 3 controls and adjusts various components inside the second MCU6.

The loudspeaker 4 plays data processed by the second MCU 6.

The first memory 5 stores data processed by the second MCU 6 and audio data.

The second MCU 6 display heart rate signals transmitted by the first MCU 9.

The low dropout regulator 7 provides a stable voltage to the first MCU 9.

The power supply 8 employs a DC 5 V adaptor or AA×3 alkaline battery.

The first MCU 9 calculates the data of the sampling module 10 and outputs the heart rate signal to the second MCU 6.

The sampling module 10 process the heart rate collected from the probe 1.

The probe 1 may be one of a blood oxygen type, a photoelectric volume type, an electrocardiographic signal type or an arterial blood pressure type.

The second MCU 6 second MCU comprises a CPU, a second memory, a sound processing circuit, and a power amplifier circuit; the heart rate signal transmitted from the first MCU is temporarily stored in the second memory, transformed by the sound processing circuit, and output to the display; the power amplifier circuit is directly connected to the loudspeaker.

The first MCU 9 comprises a CPU and an analog-to-digital (AD) conversion circuit to calculate the data of the heart rate transmitted from the sampling module; the AD conversion circuit converts an electrical signal detected by the probe into a digital signal recognizable to the first MCU.

The AD conversion circuit converts an electric signal detected by probe 1 into a digital signal recognized by the first MCU 9.

The power amplifier circuit, which is an amplifying circuit for outputting a larger power, is directly connected to and drive the loudspeaker 4.

The sound processing circuit is configured to decode and synthesize the audio data.

One side of the second MCU 6 is provided with an interface. Through the interface, the second MCU 6 is connected to an additional probe 1.

The infant sleep-inducing device further comprises a storage battery and a power interface connected to the storage battery.

A wire is arranged between the power amplifier circuit and the loudspeaker 4, and the power amplifier circuit is electrically connected to the loudspeaker 4 via the wire.

A wireless receiver is disposed in the second MCU, and the wireless receiver is in communication with a device such as a mobile phone.

First, the first MCU 9 is connected to the probe1 through the interface on one side, emphasizing that the probe1 may be the one of a blood oxygen type, a photoelectric volume type, an electrocardiographic signal type, or an arterial blood pressure type. Then, the probe 1 is used to detect the heart rate of the user the infant's mother. Next, through the AD conversion circuit, the electrical signal detected by the sampling module 10 is converted into heart rate recognizable by the first MCU 9, and then transmitted to and stored in the second MCU 6. After the type of heartbeat sound is selected with the button 3, the second MCU 6 will call the saved heart rate and the sources of heartbeat sound stored in the first memory 5, and drive the speaker to play the heartbeat sound through the power amplifier circuit.

An external sensor for testing the mother's real heart rate is provided on the infant sleep-inducing device that emits a different heartbeat sound according to the mother's heart rate, solving the problem that the existing device cannot effectively promote the infant to fall asleep.

It will be obvious to those skilled in the art that changes and modifications may be made, and therefore, the aim in the appended claims is to cover all such changes and modifications.

What is claimed is:

1. A device, comprising:
   a probe comprising a heart rate sensor detecting a signal of heart rate of a user;
   a sampling module receiving the signal of heart rate of the user and processing the signal of heart rate of the user into an electrical signal;
   a first microcontroller unit (MCU) calculating the electrical signal and outputting a heart rate data;
   a second MCU receiving and processing the heart rate data and producing an audio data of the heart rate data;
   a keyboard inputting, controlling and adjusting parameters of the second MCU:
   a display displaying an operation/control state of the device;
   a loudspeaker playing the audio data of the heart rate data;
   a first memory storing the audio data of the heart rate data;
   a low dropout (LDO) regulator providing a constant voltage to the second MCU; and
   a power supply supplying power to the probe, the sampling module, the first MCU, the second MCU, the keyboard, the display, the loudspeaker, the first memory, and the LDO regulator;
   wherein
   the first MCU comprises a first CPU and an analog-to-digital (AD) conversion circuit to calculate the electrical signal from the sampling module; and
   the AD conversion circuit converts the electrical signal into a digital signal recognizable to the first MCU.

2. The device of claim 1, wherein the heart rate sensor is a blood oxygen sensor, a photoplethysmography sensor, an electrocardiogram sensor, or an arterial blood pressure sensor.

3. The device of claim 1, wherein the power supply is a DC 5V adaptor or an alkaline battery.

4. The device of claim 1, wherein
   the second MCU comprises a second CPU, a second memory, a sound processing circuit, and a power amplifier circuit;
   the second memory is configured to temporarily store the heart rate data;
   the sound processing circuit is configured to transform the heart rate data into the audio data of the heart rate data; and
   the power amplifier circuit is directly connected to the loudspeaker.

5. The device of claim 4, wherein the second memory is a FLASH, an SD card, or a disc.

6. The device of claim 4, wherein the power amplifier circuit is electrically connected to the loudspeaker via a wire.

7. The device of claim 4, wherein the second MCU comprises an interface communicating with an additional probe.

8. The device of claim 4, wherein the second MCU comprises a wireless receiver to communicate with wireless equipment.

9. The device of claim 1, further comprising a storage battery and a power interface connected to the storage battery.

10. A device, comprising:
    a probe comprising a heart rate sensor detecting a signal of heart rate of a user;
    a first microcontroller unit (MCU) calculating the signal of heart rate of the user and outputting a heart rate data;
    a second MCU receiving and processing the heart rate data and producing an audio data of the heart rate data;
    a keyboard inputting, controlling and adjusting parameters of the second MCU;
    a display displaying an operation/control state of the device;
    a loudspeaker playing the audio data of the heart rate data;
    a first memory storing the audio data of the heart rate data;
    a low dropout (LDO) regulator providing a constant voltage to the second MCU; and
    a power supply supplying power to the probe, the first MCU, the second MCU, the keyboard, the display, the loudspeaker, the first memory, and the LDO regulator;
    wherein:
    the first MCU comprises a first CPU and an analog-to-digital (AD) conversion circuit to calculate the signal of heart rate of the user from the probe; and
    the AD conversion circuit converts the signal of heart rate of the user into a digital signal recognizable to the first MCU.

11. The device of claim 10, wherein the heart rate sensor is a blood oxygen sensor, a photoplethysmography sensor, an electrocardiogram sensor, or an arterial blood pressure sensor.

12. The device of claim 10, wherein the power supply is a DC 5V adaptor or an alkaline battery.

13. The device of claim 10, wherein the second MCU comprises a second CPU, a second memory, a sound processing circuit, and a power amplifier circuit;

the second memory is configured to temporarily store the heart rate data;

the sound processing circuit is configured to transform the heart rate data into the audio data of the heart rate data; and the power amplifier circuit is connected to the loudspeaker.

14. The device of claim 13, wherein the second memory is a FLASH, an SD card, or a disc.

15. The device of claim 13, wherein the power amplifier circuit is electrically connected to the loudspeaker via a wire.

16. The device of claim 13, wherein the second MCU comprises an interface communicating with an additional probe.

17. The device of claim 13, wherein the second MCU comprises a wireless receiver to communicate with wireless equipment.

18. The device of claim 10, further comprising a storage battery and a power interface connected to the storage battery.

* * * * *